United States Patent [19]

DeVore et al.

[11] Patent Number: 4,920,104
[45] Date of Patent: Apr. 24, 1990

[54] SODIUM HYALURONATE COMPOSITION

[75] Inventors: Dale P. DeVore, Chelmsford; David A. Swann, Lexington; Bernard P. Sullivan, Andover, all of Mass.

[73] Assignee: MedChem Products, Inc., Acton, Mass.

[21] Appl. No.: 194,187

[22] Filed: May 16, 1988

[51] Int. Cl.⁵ .................... A61K 31/715; A61K 31/73
[52] U.S. Cl. ...................................... 514/54; 514/912; 514/55
[58] Field of Search .................. 514/54, 912, 55.1; 604/28

[56] References Cited

U.S. PATENT DOCUMENTS

| | | | |
|---|---|---|---|
| 4,141,973 | 2/1979 | Balazs | 514/54 |
| 4,328,803 | 5/1982 | Pape | 514/54 |
| 4,713,375 | 12/1987 | Lindstrom et al. | 514/54 |
| 4,716,154 | 12/1987 | Mälson et al. | 514/54 |

Primary Examiner—Ronald W. Griffin
Assistant Examiner—Pamela S. Webber
Attorney, Agent, or Firm—Kane, Dalsimer, Sullivan, Kurucz, Levy, Eisele and Richard

[57] ABSTRACT

Solutions of sodium hyaluronate in physiological saline with a kinematic viscosity of from 45,000 to 64,000 cSt. are found to effect a smaller increase in post-operative intra-ocular pressure following use as an aid in opthalmological surgery, when the weight average molecular weight of the hyaluronate is within the range of from 1 to 2 million Daltons.

4 Claims, 1 Drawing Sheet

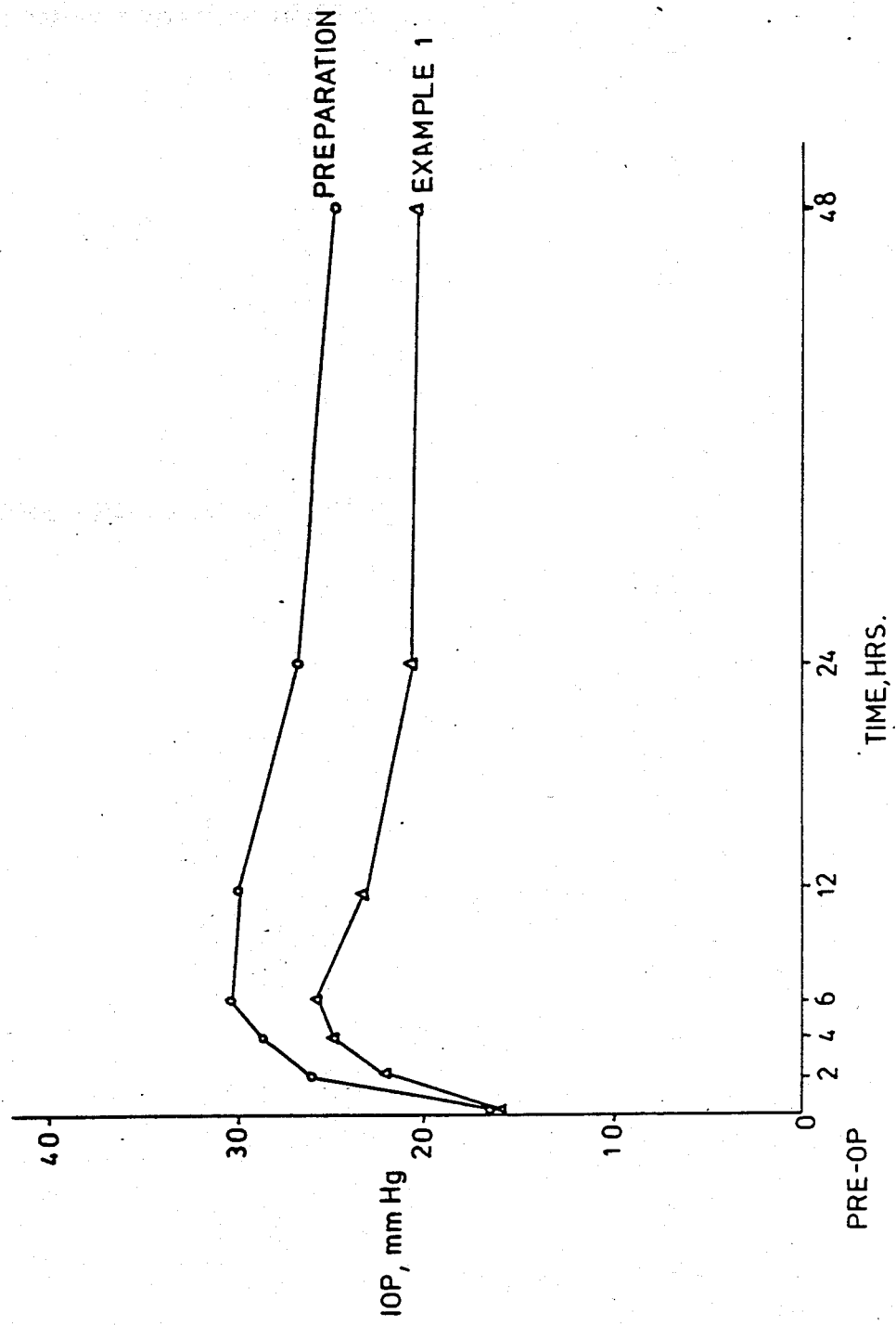

SODIUM HYALURONATE COMPOSITION

BACKGROUND OF THE INVENTION

1. Field of the Invention

The invention relates to sodium hyaluronate and more particularly to a composition of sodium hyaluronate which is useful as an aid in ophthalmic surgery.

2. Brief Description of the Prior Art

Sodium hyaluronate (NaHA) viscoelastic compositions have been employed extensively in certain ophthalmological procedures such as cataract surgery. In these procedures, the composition may be placed in the anterior chamber of the eye to facilitate surgical manipulations. Generally, the composition is partially or substantially completely removed at the conclusion of surgery; see for example U.S. Pat. No. 4,328,803 where a partial removal by dilution in-situ is suggested.

With some frequency, surgeons have observed an increased intra-ocular pressure (IOP) following surgery associated with the use of viscoelastic compositions as a surgical aid. The reason for the increase is not fully understood since transient increases occur following even routine surgical procedures where viscoelastic aids are not employed; see for example Ruiz, R. S. et al., Amer. J. of Ophthal., 103: 487–491, (1987). However, it has been suggested that IOP elevations associated with the use of a viscoelastic surgical aid composition occur when the outflow of aqueous secretions through the trabecular network is reduced. It has also been suggested that this obstruction in outflow is effected by the presence of residual molecules of the viscoelastic, exemplified by sodium hyaluronate. The relatively large sodium hyaluronate molecule may reduce flow of the aqueous secretions, when they enter the trabecular network.

Obstruction of the trabecular network may also be related to the viscosity of the viscoelastic composition, when it enters the trabecular network; see Benedetto, Ophthal. Times, April 15, 1987, p. 58. Schubert, et al., (Exp. Eye Res., 39: 137–182, 1984) reported that lower viscosity NaHA solutions (10,000 centistokes) resulted in consistently higher IOP elevation than higher viscosity solutions (40,000 cSt). They reasoned that this occurred due to the rapid dissolution of this NaHA solution causing a "traffic jam" in the trabecular network.

The importance of both viscosity and molecular weight in NaHA compositions used as aids in ophthalmological surgery, as a possible factor in post-operative IOP increases is suggested by Schubert et al., Exp. Eye Res. 39: 137–152 (1984).

Regardless of the possible mechanisms of post-operative IOP increases, the phenomena is undesired and much attention has been given to a solution to this problem, particularly as it may relate to the use of sodium hyaluronate compositions; see for example the solution posed by Pape in U.S. Pat. No. 4,328,803, who suggests an in-situ dilution of anterior chamber emplaced sodium hyaluronate.

We have discovered that a particular sodium hyaluronate composition of a particular molecular weight and viscosity may be used in ophthamological surgical procedures, and its use is associated with significantly lower increases in post-operative intra-ocular pressures (compared to use of heretofore commercially available sodium hyaluronate compositions).

SUMMARY OF THE INVENTION

The invention comprises a solution of sodium hyaluronate in physiological saline, having a kinematic viscosity within the range of from 45,000 cSt to 64,000 cSt; said sodium hyaluronate having a weight average molecular weight within the range of from 1 million to 2 million Daltons.

The solution is useful as a viscoelastic aid during conventional ophthalmalogical surgery to remove cataracts, correct glaucoma or to replace the vitreous during vitrectomy. The solution is of particular usefulness in procedures where vitreous loss occurs during surgery and there is a need for a mechanical device to push the vitreous into proper position. Intraocular hemorrhage or choroidal expulsive hemorrhage are additional examples of conditions where the compositions of the invention are usefully employed, by known procedures.

BRIEF DESCRIPTION OF THE DRAWING

The drawing is a graphical representation of IOP values observed in Example 2, infra.

DETAILED DESCRIPTION OF THE PREFERRED EMBODIMENTS OF THE INVENTION

Sodium hyaluronate of a grade and purity acceptable for a medical device is a well known compound as are methods of its preparation in a wide range of molecular weights; see for example the preparative method described in U.S. Pat. No. 4,141,973.

The compositions of the present invention may be prepared by dissolving a medically acceptable grade of sodium hyaluronate having a weight average molecular weight of from 1 to 2 million Daltons in a sufficient proportion of physiological saline to obtain a solution with a kinematic viscosity within the desired range of from 45,000 to 64,000 centistokes. Generally, the solution obtained will have a hyaluronate concentration of from about 12.0 to about 20.0 mg/ml. of solution. Alternatively, one can prepare a solution of lower viscosity and concentration than desired in the final product and then achieve a final viscosity and concentration of NaHA by evaporating water from the solution or by reprocessing the sodium hyaluronate by reprecipitation in solvent, i.e., ethanol, drying the precipitate under vacuum and then redissolving the precipitate in a suitable physiological solution, i.e., sodium chloride U.S.P. to the appropriate viscosity by adjustment of sodium hyaluronate concentration.

The method of preparing the compositions of the invention entails a simple admixture of the sodium hyaluronate in the physiological saline, preferably under aseptic conditions employing conventional mixing apparatus and technique.

Buffers, stabilizers, preservatives and sterilants may be added to the solutions of the invention as necessary or desirable, in conventional and known proportions.

The method of use of viscoelastic solutions of NaHA as an aid in opthalmological surgery is known and details need not be recited herein; see for example the procedures described in U.S. Pat. No. 4,328,803.

The following examples and preparations describe the manner and process of making and using the invention and set forth the best mode contemplated by the inventor of carrying out the invention but are not to be construed as limiting the invention. Where reported, the following tests were carried out.

MOLECULAR WEIGHT

Molecular weights reported are weight average molecular weights, determined by calculation from the limiting viscosity number using the equation of Laurent et al., Biochimica et Biophysics Acta., 42: 476–485 (1960).

Kinematic Viscosity:

Determined at a temperature of 25° C. and a shear rate of 1 sec$^{-1}$ using a Brookfield Digital Viscometer Model RVTDCP with cone spindle CP52.

Intrinsic Viscosity (I.V.)

The intrinsic viscosity was measured using a Cannon-Ubbelohde semi-micro dilution viscometer, size 75, at 37° C. and is reported in milliliters/gram (ml/g).

Preparation 1.

A quantity of sodium hyaluronate of a purity acceptable for medical use and having a calculated weight average molecular weight of $2.04 \times 10^6$ Daltons is reconstituted in sterile, pyrogen free, physiological saline to obtain a kinematic viscosity of 41,554 centistokes (cSt) and a hyaluronate concentration of 10.99 mg/ml. The solution has an intrinsic viscosity of 3012 ml/g.

EXAMPLE 1

A quantity of the sodium hyaluronate of lower weight average molecular weight, about $1.5 \times 10^6$ Daltons, is reconstituted in sterile, pyrogen-free physiological saline to yield a kinematic viscosity averaging 58,385 cSt and a hyaluronate concentration of 15.29 mg/ml. The intrinsic viscosity was 2450 ml/g.

EXAMPLE 2

A group of 60 humans at three clinical sites were selected, each requiring opthamological surgery which would be facilitated by the use of a viscoelastic solution of sodium hyaluronate. The group was divided into two subgroups of 30 each. The subjects were then operated upon using each surgeon's standard procedure. For example, the following surgical procedures being performed by Surgeon 1:

PROCEDURE: Local anesthesia was obtained with 2% Xylocaine, 0.5% Marcaine, 1:100,000 Epinephrine and 150 units of Wydase in the nadbath and retrobulbar locations of the left eye. The eye was prepped and draped in routine manner and attention directed to it.

The Schachar blepharostates were inserted. A 4-0 Bridle suture was placed underneath the tendon of the superior rectus muscle. A 180° superior peritomy was performed. Hemostasis was obtained. A partial thickness corneoscleral incision was made with a razor blade knife anteriorly with a 66-Paufique blade. The anterior chamber was entered at 12 o'clock with a razor blade knife and this was injected. Anterior capsulotomy was performed with a 30 gauge needle. Incision was carried in both directions using corneoscleral scissors. The lens nucleus was prolapsed from the eye. Cortical remnants were irrigated and aspirated from the eye. Under sodium hyaluronate the intraocular lens was inserted in the posterior chamber without difficulty. Miochol was injected and the pupil rounded nicely. Peripheral iridectomy was made at 12 o'clock. The incision was closed with 10 interrupted 10-0 nylon sutures until sphericity was documented using the Terry keratometer. The conjunctiva was tacked at 4 and 8 o'clock using 10-0 nylon sutures. A subconjunctival injection of 40 mg of Tobramycin, 500 mg of Cefadyl and 25 mg of Vancomycin was placed at 6 and 12 o'clock was well as 6 mg of Celestone at 6 o'clock. The eye was patched and shielded.

In each procedure, 0.5 ml. of a sodium hyaluronate solution was inserted into the anterior chamber during surgery. At the conclusion of surgery, Miochol was injected. The surgeon at site 1 (20 pts in each group) did not thoroughly irrigate at the completion of surgery. Surgeons at sites 2 and 3 (10 pts in each group) conducted thorough removal of the viscoelastic. In the first group of 30 patients, which functioned as a control group, the sodium hyaluronate solution employed was prepared in accordance with Preparation 1, supra. In the second group of 30 patients, the solution was prepared in accordance with the Example 1, supra.

Pre-operatively and at periodic intervals following the conclusion of surgery (2, 4, 6, 12, 24 and 48 hours) the patients intra-ocular pressure for the eye operated on was determined. The test results (mean values) are shown in the following Tables. The Table 1 shows the IOP values (mean) observed in those patients where there was an incomplete removal of the NaHA solution while Table 2 shows the IOP values (mean) for those patients where there was a complete removal. Table 3 shows the combined values.

The mean IOP values shown in the Table 3, below, are shown graphically in the accompanying drawing, over the time period of pre-operatively through 48 hours post-operatively.

TABLE 1

| | IOP Values for Site 1: Incomplete Removal | | | | | | |
|---|---|---|---|---|---|---|---|
| Solution | PreOp | 2 hrs | 4 hrs | 6 hrs | 12 hrs | 24 hrs | 48 hrs |
| Preparation 1 | 16.45 | 26.85 | 31.65 | 34.70 | 30.20 | 31.05 | 24.25 |
| Example 1 | 16.15 | 24.00 | 28.35 | 29.60 | 24.70 | 24.85 | 21.25 |

TABLE 2

| | IOP Values for Sites 2 and 3: Complete Removal | | | | | | |
|---|---|---|---|---|---|---|---|
| Solution | PreOp | 2 hrs | 4 hrs | 6 hrs | 12 hrs | 24 hrs | 48 hrs |
| Preparation 1 | 15.50 | 23.71 | 22.25 | 22.50 | 31.33 | 19.80 | — |
| Example 1 | 14.83 | 16.43 | 17.58 | 18.70 | 17.67 | 13.20 | — |

TABLE 3*

| SOLUTION | Pre-Op | Post-Op | | | | | |
|---|---|---|---|---|---|---|---|
| | | 2 Hours | 4 Hours | 6 Hours | 12 Hours | 24 Hours | 48 Hours |
| PREPARATION 1 (control) | 16.23 | 26.04 | 28.96 | 30.63 | 30.35 | 27.30 | 24.86 |
| EXAMPLE 1 | 15.85 | 22.04 | 25.68 | 25.97 | 23.78 | 20.97 | 20.71 |

*Intra-ocular pressures shown in mm Hg.

Preparation 2

A quantity of sodium hyaluronate of a purity acceptable for medical use and having a calculated weight average molecular weight of $2.65 \times 10^6$ daltons is reconstituted in sterile, pyrogen-free physiological saline to obtain a solution with a kinematic viscosity of 41,850 cSt and a hyaluronate concentration of 9.58 mg/ml. The preparation has an instrinsic viscosity of 3684 ml/g.

EXAMPLE 3

A quantity of sodium hyaluronate of lower weight average molecular weight, about $1.40 \times 10^6$ daltons is reconstituted in sterile, pyrogen-free physiological saline to yield a kinematic viscosity of 57,325 cSt and a hyaluronate concentration of 16.75 mg/ml. The preparation has an intrinsic viscosity of 2239 ml/g.

EXAMPLE 4

Samples of Preparation 2 and Example 3 were evaluated in New Zealand white rabbits. Adult rabbits (5-6 obs) were used for this aqueous replacement study. One day prior to the study, by slit lamp evaluation both eyes of each animal were examined using fluorescein dye to determine the condition of the corneal epithelium. The corneal epithelium was evaluated to determine if any corneal abrasion, ulceration or irregularities were present. On the day of the study, each animal was again evaluated prior to the injection of the test material. Fluorescein dye was not used in this pre-injection evaluation. Animals exhibiting pre-existing corneal, lens or conjunctival injury, irritation or irregularity were not used in this study.

General anesthesia was achieved by intramuscular injection of Rompun (1 mg/kg body weight) and Ketamine HCl (5 mg/kg body weight). The pupil was dilated with 0.05 ml of 1% Cyclopentolate HCl and 10% Phenylephrine HCl administered topically. One drop of proparacaine 0.5% was administered topically prior to aqueous injection. All injected solutions were sterile and administered undiluted.

The eye was prepared for surgery and a 25-gauge butterfly infusion needle was inserted at the 10 o'clock position, 0.2 mm anterior to the limbus. To prevent collapse of the anterior chamber, the outflow tubing remained capped until injection of the test material was initiated. A 1 cc syringe with a 27-gauge needle was inserted at the 2 o'clock position, 0.2 mm anterior to the limbus. The beveled edges of the needles were positioned away from the corneal endothelium. The anterior chamber was filled with 0.2 cc of the test material, the outflow and inflow needles were removed. The intraocular pressure was monitored with a pneumotonometer. IOP readings are shown below:

| Sample | IOP values (mmHg) | |
| --- | --- | --- |
|  | 24 hrs | 48 hrs |
| Preparation 2 | 17.7 | 26.4 |
| Example 3 | 10.0 | 20.0 |

Preparation 3

A quantity of sodium hyaluronate of a purity acceptable for medical use and having a weight average molecular weight of $1.8 \times 10^6$ daltons is reconstituted in sterile, pyrogen-free saline to obtain a solution with a kinematic viscosity of 36,011 cSt and a hyaluronate concentration of 11.36 mg/ml. The preparation has an intrinsic viscosity of 2790 ml/g.

EXAMPLE 5

A quantity of sodium hyaluronate preparation of Preparation 3, supra is heated by autoclave to 121° C. for 10 minutes. Following heat treatment, sodium hyaluronate is recovered by precipitation in ethanol, dried under vacuum and reconstituted in deironized, pyrogen-free water to provide a solution with a kinematic viscosity of about 30,000 cSt and a hyaluronate concentration of 25.65 mg/ml. The preparation has an intrinsic viscosity of 1350 ml/g and a calculated molecular weight of $0.73 \times 10^6$ daltons.

Samples of Preparation 3, supra and Example 5, supra, were evaluated by implantation in 5 eyes in the cat model. The controlateral eye served as the control. Measurements of IOP were made at half-hour intervals to 6 hours. Results appear below:

| Sample | Max. IOP (mmHg) | Duration Elevated IOP (Time hrs) |
| --- | --- | --- |
| Control | 14.70 | 3.5 hrs. |
| Preparation 3 | 36.67 | 4.5 hrs. |
| Example 5 | 29.00 | 3.5 hrs. |

What is claimed is:

1. A viscoelastic solution of sodium hyaluronate in physiological saline, having a kinematic viscosity within the range of from 45,000 to 64,000 cSt.; said sodium hyaluronate having a weight average molecular weight within the range of from 1 million to 2 million Daltons.

2. The solution of claim 1 wherein the kinematic viscosity is about 55,000 cSt. and the molecular weight is about 1.5 million Daltons.

3. In a method of protecting mammalian eye tissue and structures during ophthalmological surgery by introducing into the anterior segment of the eye, a viscoelastic solution of sodium hyaluronate, the improvement which comprises; using as the solution one having a kinematic viscosity of from 45,000 to 64,000 cSt. and wherein the weight average molecular weight of the sodium hyaluronate is within the range of from 1 to 2 million Daltons.

4. The method of claim 3 wherein the kinematic viscosity is about 55,000 cSt. and the molecular weight is about 1.5 million Daltons.

* * * * *